United States Patent [19]
Nkiliza

[11] Patent Number: 5,808,119
[45] Date of Patent: Sep. 15, 1998

[54] PROCESS FOR ESTERIFYING A POLYPHENOLIC OLIGOMERIC EXTRACT OF PLANT ORIGIN, COMPOSITION THUS OBTAINED AND USE THEREOF

[75] Inventor: Jean Nkiliza, Port Sainte Foy, France

[73] Assignee: Berkem, Gardonne, France

[21] Appl. No.: 518,457

[22] Filed: Aug. 23, 1995

[30] Foreign Application Priority Data

Aug. 26, 1994 [FR] France .................................. 94 10317

[51] Int. Cl.$^6$ ................................................... C07C 51/00
[52] U.S. Cl. ...................... 554/151; 554/124; 554/150; 526/1; 527/100; 527/602; 514/546; 514/552; 424/78.03
[58] Field of Search .................................... 554/124, 150, 554/151; 526/1; 527/100, 602; 514/546, 552; 424/78.03

[56] References Cited

U.S. PATENT DOCUMENTS 3,984,372  10/1976  Cottman .................................... 260/47

FOREIGN PATENT DOCUMENTS 0 252 724  1/1988  European Pat. Off. .
1 543 537  10/1969  Germany .

OTHER PUBLICATIONS

French Search Report dated May 5, 1995 in French Appl. No. 94 10317.

*Primary Examiner*—Gary Geist
*Assistant Examiner*—Deborah Carr
*Attorney, Agent, or Firm*—Staas & Halsey

[57] ABSTRACT

Process for esterifying a polyphenolic oligomer extract of plant origin by the action of an acid chloride, the compositions obtained by this process and their use in human therapy or in cosmetics are described. The extract is placed in a liquid medium which is not a solvent for the extract but which is a solvent for the ester(s) to be obtained, so as to obtain a suspension. At least one aliphatic tertiary amine of low boiling point is added to the suspension in the presence of a catalytic amount of at least one organic base other than pyridine. At least one fatty acid chloride is introduced into this mixture, the reaction mixture being stirred at a temperature below 40° C. and then concentrated by evaporation in order to obtain an esterified extract.

12 Claims, No Drawings

PROCESS FOR ESTERIFYING A POLYPHENOLIC OLIGOMERIC EXTRACT OF PLANT ORIGIN, COMPOSITION THUS OBTAINED AND USE THEREOF

BACKGROUND OF THE INVENTION

1. Field of the Invention

The invention relates to a process for esterifying a polyphenolic oligomeric extract of plant origin, especially in order to obtain saturated fatty acid esters.

2. Description of Related Art

Sparingly polymerized or nonpolymerized polyphenolic compounds of plant origin, especially hydroxycinnamic acids, flavonoids and flavanols, possess advantageous biological properties among which there may be mentioned, by way of example, a free radical scavenging effect, an antioxidant effect, an antimicrobial and antiviral effect, and a natural sunscreen effect.

Their phenolic functional groups make these compounds particularly sensitive to various degradation factors such as light, air and acidic or basic pH. In the majority of cases, this instability constitutes a restriction on the exploitation of their beneficial effects both for man and animals. The pharmacological importance of these polyphenols makes it particularly desirable to develop a means capable of imparting good stability to them which is compatible with their biological applications.

For the purposes of structural determination by nuclear magnetic resonance methods, the prior art has described the production of pure individual products by chromatography on a column of silica or on thin layer after a treatment aimed at protecting the free phenolic functions which, without this precaution, would be considerably degraded by the support. The treatment in question consists in protecting the phenolic functions by etherification or esterification, and considerably enhances the stability. Products are thus obtained which are soluble in quite nonpolar organic solvents, such as chloroform or methylene chloride. The ethers most frequently used are the methyl ethers obtained by treating the phenolic solutions either with dimethyl sulphate or with diazomethane. The esters most frequently used are peracetates prepared by the action of a mixture of pyridine and acetic anhydride in the absence of light, at room temperature for at least 24 hours or at about 80° C. for about 3 hours.

The object of the invention is to propose an economic process for the preparation of stabilized polyphenols by esterification, these products being intended for the pharmaceutical, cosmetics and food industries. According to the invention, the derivatives prepared have a high liposolubility making them compatible with the excipients of pharmaceutical dosage forms and allowing, in addition, ready regeneration of the free phenols, which form the basis of the properties sought by administration of the product.

SUMMARY OF THE INVENTION

In order to achieve the objectives defined above, it has been proposed, according to the invention, to esterify the polyphenolic extracts with fatty acid derivatives containing long hydrocarbon chains. The esters obtained are comparable in appearance to triglycerides and are soluble in solvents for fats. After administration, these esters may undergo an enzymatic hydrolysis, as for lipids, in order to regenerate the native fatty acid and the native polyphenols. In order to avoid undesirable side effects, it is proposed according to the invention to use fatty acid derivatives which are most widely distributed in the fats employed in human food, especially palmitic acid and stearic acid; in order to avoid oxidation phenomena, saturated fatty acid derivatives will preferably be considered.

It is known that a phenol may, in a known manner, be esterified according to several routes:

a) The hydroxyl compound and the carboxylic acid may be reacted together directly, at high temperature under vacuum or by catalysis with an inorganic acid, by removing the water formed via azeotropic entrainment; however, such a technique is incompatible with the low stability and the chemical behaviour of the polyphenols in question.

b) The hydroxyl compound and a carboxylic acid may be condensed together directly using a coupling agent and a weakly nucleophilic basic catalyst, the coupling agent commonly used being dicyclohexylcarbodiimide, which activates the carboxylic acid by converting it into an anhydride equivalent, and the base used generally being 4-dimethylaminopyridine; however, this technique has two major economic drawbacks:

firstly, it is expensive on account of the high price of dicyclohexylcarbodiimide, which is used in stoichiometric amount, or even in slight excess, relative to the carboxylic acid, the dicyclohexylcarbodiimide is converted into dicyclohexylurea which is insoluble in the reaction medium and is produced in an equivalent amount to the dicyclohexylcarbodiimide used. This by-product must be considered as process waste and its destruction further increases the production cost for the esters obtained by this method.

c) The hydroxyl compound may be reacted with a highly reactive derivative of the carboxylic acid, for example an acid chloride or an anhydride, in the presence of a base. The implementation of this reaction mode depends especially on the choice of the base, which acts both as a catalyst and a trap for the inorganic acid formed (HCl in the case of an acyl chloride); the reaction may be carried out in alkaline aqueous solution according to the Schotten-Baumann process. In the state of the art, it is generally proposed to use pyridine as the catalyst, the pyridine serving simultaneously as a reaction solvent, a base and a trap for the acid released by the reaction. However, on the industrial scale, the use of pyridine presents considerable drawbacks: firstly, pyridine is toxic to man and is capable of penetrating into the body by inhalation, via the cutaneous route or by ingestion, giving rise to depressive effects, hepatic and renal disorders or irritation of the skin and mucous membranes; secondly, pyridine has an unpleasant and penetrating odor, thereby requiring thorough purification of the final product by multiple washes, especially with acidified water or with a solution containing cupric ions: however, in the case of fatty esters of polyphenols, these repeated washes bring about a formation of relatively stable emulsions, thereby greatly reducing the production yield and, consequently, increasing the cost price of the corresponding esters.

The result of this analysis of the techniques, which are available to those skilled in the art and which have been summarized above, is that none of these techniques is capable at present of being used for an economic production of fatty acid esters of polyphenolic oligomers.

DESCRIPTION OF THE INVENTION

Consequently, the subject of the present invention is a process for esterifying a polyphenolic oligomer extract of plant origin by the action of an acid chloride, characterized in that the said extract is placed in a liquid medium which is not a solvent for the said extract but which is a solvent for the ester(s) to be obtained, so as to obtain a suspension; in that at least one aliphatic tertiary amine of low boiling point is added to the said suspension in the presence of a catalytic amount of at least one organic base other than pyridine; and in that at least one fatty acid chloride is introduced into this mixture, the reaction mixture being stirred at a temperature below 40° C. and then concentrated by evaporation in order to obtain an esterified extract.

In a preferred embodiment of the process according to the invention, triethylamine is chosen as the aliphatic tertiary amine; 4-dimethylaminopyridine may also be chosen as the organic base added in catalytic amount.

A chlorinated solvent such as, for example, chloroform or methylene chloride, may advantageously be chosen as reaction solvent.

The acid chloride used is advantageously a chloride of a saturated fatty acid present in natural fats, especially a chloride chosen from the group formed by palmitoyl chloride, stearoyl chloride and lauroyl chloride.

It is observed that the process according to the invention is extremely economic, given that the cost of triethylamine is considerably less than that of pyridine or of dicyclohexylcarbodiimide. Moreover, the use of triethylamine presents far fewer risks than the use of pyridine, since it is readily removed by evaporation and the residual traces are entrained by washing the product obtained with a polar solvent such as methanol, ethanol, acetone, water or mixtures thereof, for example. The 4-dimethylaminopyridine used in catalytic amount as the base is removed during the washing on account of its high solubility in the washing solvents.

The last step of the process according to the invention is a concentration, which allows the esterified extract to be obtained. This concentration may advantageously be carried out by evaporation to dryness under reduced pressure at a temperature below 40° C.; the dry product thus obtained may be purified by washing, preferably by several successive washes, with at least one polar solvent such as methanol, ethanol, acetone, water or mixtures thereof. After such a washing, the product is dried at a temperature below 40° C., it being possible for this drying to be performed in the open air, or under vacuum, or in a ventilated oven.

Given their enzymatic hydrolysis in the body, the esterified polyphenols thus obtained retain the usual applications of polyphenolic extracts in the native state; they may be administered topically in cosmetics or topically or orally in human therapy.

In order to gain a better understanding of the subject of the invention, an embodiment thereof will now be described, purely by way of illustrative example and with no limitation being implied.

EXAMPLE 100 grams of polyphenolic oligomers extracted from grape seeds are suspended in 600 ml of chloroform. 250 ml of triethylamine and a catalytic amount of 7 grams of 4-dimethylaminopyridine are added to this suspension. This mixture is stirred mechanically under nitrogen and 400 ml of palmitoyl chloride are introduced slowly. When the addition is complete, the mixture is stirred at room temperature for 12 hours. After this reaction period, the mixture is evaporated to dryness under reduced pressure, while maintaining the temperature below 40° C.

The residue is then taken up in 1 liter of a methanol/water (9/1) mixture. The mixture is stirred for 1 hour at room temperature, the supernatant is separated off, 1 liter of methanol is then added and the stirring is continued at room temperature for 1 hour. This mixture is filtered and the solid is washed with acetone and then dried.

The product obtained after drying is in the form of a powder of fatty consistency, which is insoluble in polar solvents and soluble in solvents for fats, such as hexane or chlorinated solvents, for example. The infrared spectrum, acquired on a film left by evaporation of the chloroform on an NaCl disc, indicates the ester functions by an absorption band at 1725 cm$^{-1}$; the absence of an absorption band between 3600 and 3100 cm$^{-1}$ indicates the absence of free hydroxyl groups. The ultraviolet spectrum has an absorption maximum at about 273 nanometers.

I claim:

1. A process for esterifying a polyphenolic oligomer extract of plant origin by the action of an acid chloride, wherein said extract is placed in a liquid medium which is not a reaction solvent for said extract, but which is a reaction solvent for the ester(s) to be obtained, so as to be obtain a suspension, wherein at least one aliphatic tertiary amine having a low boiling point is added to said suspension in the presence of a catalytic amount of at least one organic base other than pyridine, forming a reaction mixture, and wherein at least one fatty acid chloride is introduced into said reaction mixture, said reaction mixture being stirred at a temperature below 40° C. and then concentrated by evaporation to obtain an esterified extract.

2. The process according to claim 1, wherein triethylamine is chosen as said aliphatic tertiary amine.

3. The process according to claim 1, wherein 4-dimethylaminopyridine is chosen as said at least one organic base.

4. The process according to claim 1, wherein a chlorinated solvent is chosen as said reaction solvent.

5. The process according to claim 4, wherein said chlorinated solvent is chosen from the group formed by chloroform and methylene chloride.

6. The process according to claim 1, wherein said at least one acid chloride is chosen from the group formed by the chlorides of saturated fatty acids present in natural fats.

7. The process according to claim 1, wherein said at least one acid chloride is chosen from the group formed by palmitoyl chloride, stearoyl chloride and lauroyl chloride.

8. The process according to claim 1, wherein the concentration of the esterified extract is carried out by evaporation to dryness under reduced pressure at a temperature below 40° C.

9. The process according to claim 1, wherein said esterified extract obtained after concentration is purified by washing with at least one polar solvent, followed by drying at a temperature below 40° C.

10. A composition of a polyphenolic oligomer derived from an extract of plant origin and esterified by fatty acid chloride obtained by the process according to claim 1.

11. A process comprising the step of:

using in a cosmetic, topically or orally, a composition of a polyphenolic oligomer derived from an extract of plant origin esterified by fatty acid chloride according to claim 10.

12. A process, comprising the step of:

using in a pharmaceutical, topically or orally, a composition of a polyphenolic oligomer from an extract of plant origin esterified by fatty acid chloride according to claim 10.

* * * * *